United States Patent [19]

Gaafar

[11] 4,241,045
[45] Dec. 23, 1980

[54] **PURIFIED ANTIGEN TO TEST FOR *NEISSERIA GONORRHEAE* ANTIBODIES**

[75] Inventor: Hassan A. Gaafar, Voorheesville, N.Y.

[73] Assignee: Research Corporation, New York, N.Y.

[21] Appl. No.: 905,954

[22] Filed: May 15, 1978

[51] Int. Cl.$^2$ .................... G01N 33/16; A61K 43/00
[52] U.S. Cl. .................................. 424/1; 260/112 R; 424/12; 435/7
[58] Field of Search ............. 424/1, 12; 195/103.5 A; 260/112

[56] References Cited

PUBLICATIONS

Cohen, J. of Bacteriology, vol. 94, No. 1, Jul. 1967, pp. 141–148.

*Primary Examiner*—Benjamin R. Padgett
*Assistant Examiner*—Christine M. Nucker
*Attorney, Agent, or Firm*—Cooper, Dunham, Clark, Griffin & Moran

[57] ABSTRACT

Serological method for determining the presence of *Neisseria gonorrhoeae* antibodies in human sera and products utilized in such testing.

17 Claims, No Drawings

PURIFIED ANTIGEN TO TEST FOR *NEISSERIA GONORRHEAE* ANTIBODIES

RELATED APPLICATION

Subject matter relating to this application appears in copending application Ser. No. 831,128 filed on Sept. 7, 1977.

FIELD OF INVENTION

This invention relates to methods and products useful for determining the presence of *Neisseria gonorrhoeae* antibodies in human sera by serological methods.

BACKGROUND OF INVENTION

The present mass screening method for the detection of gonorrhea is a bacteriological method. It requires two to seven days for completion because it necessitates waiting for growth of a colony of gonococcus organisms in an appropriate culture medium and confirmatory biochemical reactions by growth in a fermentation medium, such as shown in Table I. Moreover, the bacteriological method requires that a specimen of the gonorrhea caused discharge arrive at the testing laboratory with the fragile gonococcus organism still viable, a natural time limit of as little as two days. There is real need for improvement.

A serological method which would be capable of detecting antibodies in a blood sample would be highly desirable for use in a mass screening program to demonstrate that an individual may be currently suffering from gonorrhea or had been infected in the past. Individuals reacting positively could then be tested by the bacteriological method to determine if the infection is current. Several serological methods have been reported, but none is completely satisfactory. The primary reason for dissatisfaction has been the low sensitivity and the high number of false positive reactions.

A serological method has been developed which substantially alleviates the difficulties with known serological techniques, and is suitable for use in mass screening programs as an adjunct to the bacteriological method with substantial elimination of false positive reactions. This method is described and claimed in the above identified patent application.

This method is based upon the discovery that *Neisseria gonorrhoeae* (N.g.) organisms produce a species specific antigen which when present on the whole cell or in crude extracts is inactivated by heat and is trypsin sensitive. The antigen reacts specifically with antibodies in patients sera which are produced as a result of an infection elicited by N.g. organisms. This interaction can be demonstrated by any of several techniques normally employed for these purposes. Most of them are discussed in the aforesaid application.

This antigen which has been called L-antigen, has been extracted as an L-antigen preparation or composition by a mild detergent procedure, and its characteristics described in an article by Chen N. C., Karmei K., Zucherman J., and Gaafar H. A., which was published in Infection and Immunity Vol. 18, p. 230–236. Another procedure which resulted in the preparation of an antigen immunologically indistinguishable from that prepared by the detergent procedure was described by Schraeder, Janet A., and Gaafar, H. A. published in Health Laboratory Science Vol. 15, p. 15–21.

The forms of L-antigen isolated by the described procedure show the following common characteristics:
1. Specie specificity
2. The antigen mixture contains protein and carbohydrate.
3. Heat lability in aqueous media. The ability to react with specific antibodies present in infected patients' sera is reduced or eliminated by heating at 100° C. for 1 hr.
4. Stable in aqueous media at pH values of 3–11.
5. Soluble in aqueous media at low concentration but insoluble in methanol, chloroform and acetone.
6. Reacts with specific rabbit anti-human serum.

The preparation described by Chen et al. has these additional characteristics:
1. Trypsin sensitive
2. Resistant to dextranese, neuraminidase, DNA-ase, and RNA-ase.
3. A molecular weight of antigenically active subunit of 37,000–40,000 as determined by SDS-PAGE.

On the other hand, the antigenic preparation of Schrader et al. had higher carbohydrate content, and was trypsin resistant.

These data confirmed that the physical characteristics of the partially purified L antigen are dependent on the method of extraction and purification and implies that these preparations contain other factors which affect the detectability of the L-antigen.

These antigenic preparations are useful for serological testing in accordance with procedures described in the aforementioned patent application such as indirect immunofluroescence, agglutination, enzyme linked immunsassay, radio-immunoassay, complement fixation tests, precipitation, and countercurrent immunoelectropheresis. The specificity of the tests is improved by prior heating of the patient serum to inactivate the naturally occuring antibodies which might react with the contaminating factors in the antigen preparation and/or by prior absorption of the serum with a sorbent made of N. Meningitides cells as described in U.S. Pat. No. 4,029,756.

THE INVENTION

A procedure has now been discovered which permits the isolation of purified L-antigen preparation which is more heat stable and which can be used in serological testing with a specificity of 85–90% or higher without the need for heating the serum.

The key to this procedure is the discovery that contaminating proteins and carbohydrate can be removed by a two step procedure involving precipitation of the contaminating proteins with trichloroacetic acid and removal of the carbohydrate by ultrafilteration through an Amicon X-100 filter (p-10 to X-300 filters can be used). The purified "L" antigen is found in the retentate and has the following characteristics:
1. It stimulates the production of specific antibodies when used to immunize rabbits. The antiserum produced reacts with "L" antigen specifically irrespective of its stage of purity or method of extraction. This antiserum will produce only one precipitin line against "L" antigen preparations in immuno diffusion, countercurrent, or two dimensional immunoelectrophoresis.
2. It is more resistant to heat. It retains activity even after boiling in water for 1 hr. In this application, this antigen preparation is referred to as heat resistant to differentiate it from the more heat labile forms previously described.
3. stable when incubated with the following enzymes:
   DNA-ase
   RNS-ase
   dextransase
   neuraminidase
   lysosyme,
4. inactivated when incubated with trypsin,
5. molecular weight of active subunits of 37,000–40,000 as determined by SDS-polyacrylamide gel,
6. isoelectric point of 4±0.2,
7. contains 2–3% organic phosphorus,
8. soluble in aqueous media containing surface active agents, and insoluble in methanol, chloroform, and acetone, and
9. reacts specifically with antibodies produced in rabbits against purified L-antigen.

By "heat stable", it is meant that the antigen composition can be boiled in water for at least one hour without destroying its ability to react with its complementary antibody.

Before continuing with this description, it will be helpful to describe what is meant by certain of the terms used to refer to the various forms of L-antigen preparations as used in this description of the invention.

Heat labile L-antigen refers to the heat labile product isolated in accordance with the above-identified patent application. Besides heat lability, it differs from other L-antigen preparations by the presence of 1–10% of carbohydrate and other factors. Heat stable L-antigen refers to the product isolated in accordance with this invention. It differs from heat labile L-antigen in that it contains less than 1% carbohydrate, and, in fact, may be essentially carbohydrate free.

Purified L-antigen refers to the product used to immunize rabbits to produce the anti-serum or antibody which reacts specifically with L-antigen.

For a proper understanding of this invention it is necessary to understand the function of "purified L-antigen". This product, prepared as described below, is used to stimulate in rabbits the production of antibodies which are specific for L-antigen.

The exact reason for the difference in functionality between heat labile L-antigen and heat stable L-antigen is not completely understood, although it is clear that both compositions contain exactly the same L-antigen. A logical explanation is possible, however, although this invention should not be limited by theory.

It is possible that heat labile L-antigen as isolated in various preparations is associated with a number of other materials, principally carbohydrate in nature, although some are clearly proteins. They may also be associated with artifacts from the method of preparation, such as SDS if this detergent is employed. This association may be actual chemical bonding by classical ionic or covalent bonding, or it may be a looser type of bonding such as hydrogen bonding or Van der Vaal's forces. These associated materials may be called antigen factors.

Human serum may contain a number of antibody factors which will react with the associated antigen factors and cause false positive reactions. These antibody factors may be heat labile, or reactive with Neisseria meningitides (N.m.) antigens. Thus if the serum to be tested is initially heated, or absorbed with N.m. antigen, the antibody factors are removed, and are not available to react with the antigen factors.

Another possibility, in accordance with this theory, for avoiding the necessity of preheating or preabsorbing the sera is to remove the antigen factors. It is believed that the treatment with trichloroacetic acid removes these factors.

It is surprising to find that trichloroacetic acid will fractionate heat labile L-antigen to produce a solution containing heat stable L-antigen. Both forms of L-antigen are proteins, and trichloroacetic acid is classically utilized to separate protein from cosolution with other materials by selectively precipitating the protein. For this use it is normally employed at volume concentrations of more than 10%. It has been found, however, in accordance with this invention that at concentrations below the normally employed concentrations, trichloroacetic acid will selectively precipitate those factors which are associated with the heat lability of previously known L-antigen preparations. The preferred range for effecting fractionation is from 5% to 10% by volume. At lower concentrations the fractionation is less effective, and at higher concentrations appreciable quantities of heat stable L-antigen will precipitate.

The optimum sources of antigen for the process of this invention are Neisseria gonorrhoeae B-585, B-370 and B-1094. These organisms have been deposited at the American Type Culture Collection, and have received the accession numbers 21823, 21824 and 21825 respectively. Their taxonomic description is:

| Order: | Eubacteriales |
| Family: | Neissericeae |
| Genus: | Neisseria |
| Species: | Gonorrhoeae |

Morphology

Gram negative spherical or bean shaped diplococci with adjacent sides flattened usually $0.6 \times 1.0\mu$ and more uniform in size.

Biochemical and Cultural

Aerobic, optimal growth requires 4–10% $CO_2$ and incubation at 36° C.

The cultures grow slowly on chocolate agar producing small barely visible colonies after 24 hours (0.1 Mm in diameter) with typical morphology seen on 48–72 hours cultures. The colonies are small 1.0 Mm in diameter, gray white, transparent, smooth, with round entire edge, glistening surface and butyrous consistency. B-1094 produced slightly larger colonies and grows more rapidly.

Oxidase+, catalase+; ferments glucose but not maltose, lactose or sucrose.

Antigenicity

All three isolates share common antigens which have been designated 'L' and are utilized in the practice of this invention.

Virulence

All three strains were originally isolated from patients with symptomatic gonorrhea.

In the process of the invention the sera to be tested is first diluted in physiological saline solution at a dilution of from about 1:2 to 1:1000.

Typically useful Fermentation, Growth and Maintenance medium are illustrated in Tables I, II, III, and IV below.

TABLE I
FERMENTATION MEDIUM

Starch gelatin agar, infusion-free, with indicator and carbohydrate (for *Neisseria gonorrhoeae* and *Neisseria meningitidis*)

| | |
|---|---|
| Agar | 6 grams |
| Gelatin | 10 grams |
| Sodium chloride | 5 grams |
| Peptone (Difco proteose No. 3) | 10 grams |
| Starch, soluble, powdered | 5 grams |
| Water to Make | 1000 grams |
| Phenol red, 0.02 percent | 30 ml. per kg. |
| Carbohydrate (Sucrose, Glucose or Maltose) | 10 grams per kg. |

Dissolve the agar in half the water by autoclaving; the gelatin, salt, peptone, and starch in the remainder with heat. Combine and make up to total weight. Adjust pH to 7.4–7.6. Filter through cotton. Weigh the filtrate recovered and add the indicator and carbohydrate. Dispense 2.5 ml. amounts in 11 by 75 mm. tubes and autoclave at 115° C. for twelve minutes. Trim the plugs and seal with paraffin.

TABLE II
GROWTH MEDIUM

Glucose agar, infusion free, with coagulated blood (for *Neisseria gonorrhoeae* and *Neisseria meningitidis*)

| | |
|---|---|
| Agar | 15 grams |
| Sodium chloride | 5 grams |
| Disodium phosphate, $Na_2HPO_4$ | 5 grams |
| Peptone, (Proteose peptone #3) | 20 grams |
| Glucose | 0.5 grams |
| Distilled water to make | 1000 grams |
| Rabbit blood, defibrinated, sterile | 10 ml. per 100 |

Dissolve the agar in half the water by autoclaving; the salts, peptone, and glucose in the remainder with heat. Combine and make up to 1 kg. and adjust pH to 7.4–7.6. Dispense 1500 ml. amounts in 3 L gauged neck flasks. Autoclave thirty minutes. Store.

As required, melt the agar base. Admix the blood aseptically 15–20 ml. amounts in glass-covered Petri plates. Deliver without incubation.

TABLE III
MAINTENANCE MEDIUM

Beef-infusion agar with ascitic fluid

| | |
|---|---|
| Beef infusion, concentrated | 500 grams |
| Agar | 5 grams |
| Sodium chloride | 5 grams |
| Peptone | 10 grams |
| Water | 500 grams |
| Ascitic fluid, sterile | an equal volume |

TABLE IV
CHARCOAL GROWTH MEDIUM

| | |
|---|---|
| Difco GC Medium Base | 36.0 grams |
| Isovitalex | 10.0 ml |
| Fisher Scientific neutral activated decolorizing charcoal | 5.0 grams |
| Distilled water | 1000 ml |

Dissolve the agar in the water by autoclaving, and the peptone and salt in the infusion. Combine. Make up to total weight. Adjust pH to 7.5 with 1 N NaOH. *Filter by asperation.* Usually dispense 400 ml. amounts in 2 liter flasks and autoclave thirty minutes. Store. Melt the agar base and cool to 50° C.

Warm the ascitic fluid to 50° C. and combine aseptically. Mix well and dispense with aseptic precautions 4–6 ml amounts in 15 by 125 mm tubes. Cover the medium aseptically with about 4 ml of sterile mineral oil. Cool in an upright position. Incubate forty-eight hours at 35° C. −57° C. and ninety-six hours at 20° C.-27° C. Inspect and store.

In the presently preferred procedure for purification of the purified L-antigen and heat stable L-antigen of this invention, the selected N.g. strains are grown on a suitable media, preferably Rabbit chocolate agar described above. They are subcultured in 200 ml. tissue culture bottles each containing 80 to 100 ml. of charcoal medium. After 18 to 24 hours, the growth from the bottles is used to seed covered metal trays containing about one liter of charcoal medium. After 18 to 24 hours incubation the cell growth is suspended in physiological saline solution and filtered through sterile gauze. During this and all subsequent manipulations involving the antigen or fractions containing the antigen unless noted otherwise, the solutions, suspensions, etc. are kept cold at about 5° C. to 10° C.

The residue on the filter is washed with physiological saline and centrifuged at about 10,000 RPM for about 15 minutes. The centrifuged material is decanted and the supernatant liquid discarded. The sediment is resuspended in physiological saline, pooled and washed by centrifugation.

The antigen may be extracted with cationic detergents such as sodium lauryl sulfate (SDS), sodium deoxycholate, sodium cholate or similar detergents, or with inorganic salt solutions such as aqueous solutions of lithium acetate, or potassium or sodium chloride. It is preferred to use inorganic salt solutions for extraction since it has been observed that detergent materials, particularly SDS cling tenaciously to the L-antigen and interfere with those tests in which the antigen must be absorbed to a surface such as the enzyme linked immunoassay test (ELISA), or the radioimmunoassay test (RIA).

A typical procedure for the preparation of heat stable L-antigen using a detergent is shown in Example I. Example II shows the procedure for the preparation of heat stable L-antigen using an inorganic salt solution. Example III illustrates the procedure for the preparation of purified L-antigen used to immunize rabbits for the preparation of antibodies specifically for heat stable L-antigens.

It will be noted that the characteristics of the isolation procedure are:

1. Forming a cell pellet of N.g. cells and extracting.
2. Passing resulting extract over a molecular sieve column. It has been observed that the most useful sieves are those with an exclusion limit of at least 200,000. The L-antigen is always found in the void volume.
3. Adding trichloroacetic acid.
4. Separating the precipitate.

The solution remaining after separation of the precipitate can be treated to isolate the heat stable L-antigen, or it can be concentrated to produce useful concentrations of heat stable L-antigen. The concentrationed solutions can be used to immunize rabbits or can be used for testing human sera. The protein concentration of useful solutions as measured by the Lowry method is normally from 25 μg/ml to 1.0 μg/ml, but it may be higher.

The heat stabile L-antigen preparation of this invention can be utilized in a variety of procedures to determine the presence or absence of N.g. antibodies in human sera. In all of these tests the sera to be tested is used directly or diluted in physiological saline or other diluent to a dilution of from 1:2 to 1:1000 and incubated with the heat stabile L-antigen. The separate tests are utilized to measure the presence or absence of an antigen-antibody conjugate.

Typical tests which can be employed with the heat stabile L-antigen preparation include radioimmunoassay, ELISA, precipitation, agglutination, complement fixation, and immunofluorescence.

If the preparation is obtained by an inorganic salt procedure, the antigen may be absorbed directly on solid phase carriers such as the walls of a glass or plastic tube or particulate carriers such as polystyrene beads or lecithin cholesterol. Several of these procedures are illustrated in the examples. Those skilled in this art will have no difficulty in understanding the application of those other procedures which are not specifically illustrated.

Basically, the test method of this invention comprises the detection of a conjugate formed by reaction between the N.g. produced antigen and complementary antibody. Detection may be direct as by precipitation or agglutination tests or by reaction with an anti-human IgG labeled with an element or chemical which is detectable by a chemical or physical method, although either the antigen or the antibody can be similarly labeled.

The antigen or the antibody may be chemically conjugated to or physically adsorbed on an insoluble particulate carrier. Adsorbents include, for example, lecithin-colesterol and various polymer latices such as a polystyrene latex, polycarbonate, bentonite, charcoal or red blood cells. The particles comprising antigen adsorbed on an adsorbent are then mixed with the sera to be tested and the presence or absence of flocculation or clumping noted. The sensitivity of this procedure can be enhanced by washing the particles to remove unreacted protein followed by the addition of anti-human IgG. Positive reactions give clumps while the negative reactions the antigen coated particles remain homogeneously dispersed.

A typical agglutination test in which the antigen is adsorbed on charcoal may be conducted as follows:

The antigen is diluted with saline and mixed with an aqueous suspension of fine charcoal particles by adding one volume of charcoal (2.5 mg/ml) to 8 volumes of antigen in a tube. The reagents are mechanically agitated using a Vortex mixer for 5 min. at room temperature and brought to 10 volumes with glycine buffered saline, pH 8.2 (73.1 g glycine, 50 g NaCL, 10 g bovine serum albumin, and 35 ml of 1.0 N sodium hydroxide per 1000 ml). The sera to be tested are diluted 1:10 in physiological saline and kept at 59° C. for 30 min. The serum (0.05 ml) is placed in a circle printed on a plastic-surfaced card, and spread within the circle with a wooden toothpick. Sensitized charcoal (0.016 ml), prepared as above, is then added, and the card rotated for 8 min. at 180 rpm, hand-tilted, and left horizontal for 2 min. The results may be read under direct light using a 10x magnifying lens. The agglutination is fine, and any degree of agglutination may be considered positive.

The anti-human IgG, antigen or antibody can be labelled with a radioactive element, an enzyme or a fluorescent material. The radioactive label can be detected by any of the currently available counting procedures. The preferred isotope labels are $14_C$, $131_I$, $125_I$ and $35_S$. The enzyme label can be detected by any of the presently utilized colorimetric, spectrophotometric, fluorospectrophotometric or gasometric techniques. The enzyme is conjugated to the anti-human IgG by reaction with bridging molecules, such as carbodiimides, diisocyanates, glutaraldehyde and the like. Many enzymes which can be used in these procedures are known and can be utilized. The preferred are peroxidase, B-glucuronidase, B-D-glucosidase, B-D-galactosidase, urease, glucose oxidase plus peroxidase, galactose oxidase plus peroxidase and acid phosphatase. Fluorescent materials which may be used include, for example fluorescein, rhodamine and auramine.

EXAMPLE I

Preparation of "Heat Stable" Antigen Using Detergent

1. *Neisseria gonorrhoeae* ATCC 21824, is grown on rabbit chocolate agar slants for 18–24 hours at 37° C. in a 4–8% $CO_2$ atmosphere. The growth is subcultured to 800-ml (29 ounce) tissue culture bottles each containing 80–100 ml of charcoal medium (Table IV). After 18–24 hours the growth is harvested and used to seed metal trays containing about 1 liter of the charcoal medium. After incubation for 18–24 hours, the cells are harvested and suspended in sterile physiological saline. The cell suspension is checked for gross contamination by Gram stain, filtered through sterile gauze and centrifuged at 10,000 Xg in Sowal RC2-B for 10 minutes. The pellet is then suspended in 0.3% sodium dodecyl sulfate (SDS) in physiological saline at 0.25 g (wet weight) per ml. The suspension is homogenized gently with a wooden applicator stick for 10 minutes at room temperature and then centrifuged at 12,000 Xg for 10 minutes. The supernatant was decanted and the pellet re-extracted with 0.1% SDS as above. Both supernatants are pooled and centrifuged at 17,000 Xg for 10 minutes to remove the residual cells. This product is labelled Crude Extract.

The Crude extract is fractionated by passing 400–600 ml (4–5 mg of protein/ml) through a membrane filter (Amicon XM—100A) at room temperature. The filtrate is discarded and the retentate recovered in 70–100 ml of 0–15% SDS solution.

This product is placed on a Sepharose 4B column equilibrated with 2 mM sodium phosphate buffer, pH 7-6 and eluted with the same buffer at 5° C. The antigen appeared in the excluded volume.

The antigen rich fractions from 4B Sepharose are combined and concentrated to 0.1 its volume by disalysis against Ficoll (Pharmacia Fine Chemicals). This product which is referred to as the concentrated 4B fraction is then frozen in liquid nitrogen and thawed. The resulting suspension is treated with a mixture of Triton X-100 and EDTA pH 7-6 at a final concentration of 1.5% and 10 mM respectively. After 3 hours incubation at room temperature and centrifugation at 100,000 Xg for 1 hour at 5° C., the supernatant is decanted and is referred to as the "soluble antigen".

The soluble antigen is chromatographed on DEAE-cellulose column equilibrated with 0.01 M sodium phosphate buffer pH 7-6 containing 0.5% Triton X-100, and developed stepwise with buffers with molarity of 0.01, 0.05, 0.1, 0.2, and 0.3. The antigen rich fractions of each peak are pooled, concentrated, dialyzed against saline, and then fractionated by adding cold trichloroacetic acid (TCA) to a final concentration of 10%, mixed and centrifuged at 5000 rpm for 5 minutes. The supernatant is dialyzed against saline and concentrated by dialysis against Ficol. The dialysate is then filtered through a membrane filter (Amicon PM-30) at room temperature to remove contaminating polysacharide.

The retentate is the purified "L" antigen and it may be recovered in saline or 0.06 M carbonate buffer pH 9.0 containing 0.02% $NaN_3$.

EXAMPLE II

Preparation of "Heat Stable" of Antigen Using Inorganic Salt Lithium Acetate

1. The organism is grown as in Example I.
2. The cell pellet is homogenized in 200 mM lithium acetate buffer pH 6.0 with 10 mM EDTA at 0.166 g (wet weight) per ml, and shaken at 45° C. for 2 hours.
3. The cells are removed by centrifugation at 12,000 X g for 10 minutes. The supernatant is chromatographed on Sepharose 4B column equilibrated with 2 mM sodium phosphate buffer pH 7-6 and 0.01% sodium ozide and eluted with the the same buffer. The "L" antigen activity was found in the excluded volume.
4. Concentrate by dialysis against Ficoll and centrifuge at 100,000 X g for 1 hour at 5° C.
5. The supernatant is dialyzed against 0.01 M sodium phosphate buffer pH 7.6 for 48 hours and chromatographed on a DEAE-cellulose column equilibrated with the same buffer. The column was developed stepwise with sodium phosphate buffer 0.01 M pH 7-6, 0.05 M ph 7-4, and 0.1 M pH 7-2 followed by potassium phosphate buffer 0.2 M pH 7-0 and 0.3 M pH 6-8. The antigen is found mainly in peaks 3 and 4.
6. The peaks with highest antigen activity are then pooled, concentrated, fractionated by TCA as in Example I and filtered through an Amicon filter PM-30 and the retentate treated as in Example I to obtain the desired product.

EXAMPLE III

Preparation of Specific Antiserum

Purified L-antigen from either detergent or salt extraction is incubated at 56° C. for 30 minutes in a solution of 27 mM tris (hydroxymethyl) methylamine acetate buffer pH 6.4 containing 27 mM dithiothreitol, 0.66 mM EDTA, and 0.7% (W/Vol) SDS and applied to a Bio-Phase 7-5% polyacrylamide gel. The sample is then run at room temperature at 8 MA/gel for 2 hours. One gel is stained to identify the different bands. The slowest migrating band (EA. Mol. wt. 38,500) is extracted from the SDS-PAGE gel and used to immunize inbred chinchilla—Flemish rabbits. The rabbits are infected with 2.0 ml of antigen preparation (25.0 Mg of protein) in complete Freunds adjuvant followed by two booster injections in saline at weekly intervals. The rabbits are bled 10 days after the last injection and methiolate is added to the serum at a final concentration of 1:5000.

This serum detects the presence of L-antigen in any preparation when present in concentrations as low as 1 to 5 $\mu$g/ml.

EXAMPLE IV

Elisa Test (Microplate)

A. Preparation of microtitration plates a. Disperse 0.2 ml of an antigen composition with a concentration of 5 $\mu$g/ml into 94 of 96 wells in a standard microtitration plate.
b. Seal plate and incubate it for 3-24 hours at 37° C. in a water bath or an incubator.
c. The plates may be used immediately or stored at 4° C.

B. Preparation of Substrate
Stock Solution
1% W.V. O-phenylenediamine hydrochloride in water or 1% W/V 3.3'-dimethoxybenzidine in methanol. Store in dark container.
Working Solution
Prepare immediately before use. 1 ml stock solution+96 ml distilled $H_2O$ add 0.1 ml 3% $H_2O_2$—mix thoroughly.

C. Execution of the Test
1. Remove antigen solutions from wells (it may be reused to sensitize additional plates).
2. Wash each well 3× with PBS containing 0.05% Tween 20 (PBS/T).
3. Prepare 1:4 dilution of each serum in PBS/T and dispense 0.2 ml of the diluted serum in each of the first 92 wells.
   Wells 93, 94, 95, and 96 are used as controls.
   Well 93 Positive Serum Control
   Well 94 Negative Serum Control
   Well 95 (No antigen)+Positive Serum
   Well 96 (No antigen)+Negative Serum
4. Incubate at 37° C. for 30 min.
5. Remove sera from all wells and wash with PBS/T 3×.
6. Add 0.2 ml of working dilution of horse radish peroxidase conjugated anti-human IgG (1:100-1:10,000).
7. Incubate at 37° C. for 30 min.
8. Remove conjugate and wash as before.
9. Add 0.2 ml working solution of substrate to each well and let stand at room temperature (Protected from light) for 30 min.-1 h.
10. Add 0.05 ml of concentrated HCl to each well to stop the reaction and develop color.
11. Read the results visually against white background or
    Read in a spectrophotometer at 540 nm N.B. This test is designed for screening at one dilution but it could be used as a quantitative test to determine the titer and monitor the change in antibody level during the course of the disease.

The results of a series of tests are shown below. In the tests culture positive and culture negative samples were tested in both the ELISA test and fluorescent gonorrheae test—heated (FGT-H) described in patent application serial number 831,128 referred to above.

TABLE IV

|  | No. | ELISA Positive | % | ELISA Negative | % |
|---|---|---|---|---|---|
| Culture positive | 32 |  |  |  |  |
| FGT-H positive | 26 | 24 | 92.3 | 2 | 7.7 |
| FGT-H negative | 6 | 2 | 33.3 | 4 | 66.7 |
| Culture negative | 65 |  |  |  |  |
| FGT-H positive | 30 | 15 | 50 | 15 | 50 |
| FGT-H negative | 35 | 0 | 0 | 35 | 100 |

The results are shown in Table V.

TABLE V

| | No. | ELISA | % Positive |
|---|---|---|---|
| Culture Positive | | | |
| FGT-H positive | 113 | 109 | 97 |
| FGT-H negative | 61 | 35 | 57 |
| Culture Negative | | | |
| FGT-H positive | 286 | 81 | 28.0 |
| FGT-H negative | 596 | 18 | 3.0 |

EXAMPLE V

Elisa Test (Coated Tube Test)

A. Preparation of Coated Tubes
a. Dispense 0.2 of antigen composition with same concentration as in previous example into each tube.
b. Incubate it 3-24 hours at 37° C. in a water bath or an incubator, then place at 5° C. for 2 days.
c. The tubes are emptied by suction and either used immediately or stored at −20° C. until needed.
B. Preparation of Substrate
Same as in Example IV
C. Execution of the Test
1. Remove antigen solution from tubes.
2. Wash each tube 3× with PBS containing 0.05% Tween 20 (PBS/T).
3. Place 100 μl of PBS/T in each tube.
4. Add one drop of undiluted human serum (Ca 25 μl)-Mix.
5. Incubate at 37° C. for 1 h.
6. Remove the serum and wash 4× with PBS/T.
7. Add 100 μl of working dilution (1:100–1:10,000) of anti-human IgG conjugated to horseradish peroxidase.
8. Incubate at 35° C. for 1 h.
9. Wash 5× with PBS/T.
10. Add 300 μl of the working dilution of substrate and let stand at room temperature (protected from light) for 1 h.
11. Add 200 μl of 6 N HCl.
12. The results are read visually or spectrophotometrically at 540 nm.

The results are shown in Table VI.

TABLE VI

| | No. | RIA Positive | % Positive |
|---|---|---|---|
| Culture Positive | | | |
| FGT-H Positive | 6 | 6 | 100 |
| FGT-H Negative | 22 | 16 | 73 |
| | 28 | 22 | |
| Culture Negative | | | |
| FGT-H Positive | 19 | 11 | 58 |
| FGT-H Negative | 82 | 8 | 10 |

EXAMPLE VI

Ria Test

Step A is the same as in Example V.
C. Execution of the Test
1. Remove antigen solution from tube.
2. Wash each tube 3× with PBS containing 0.05% Tween 20 (PBS/T).
3. Place 100 μl of PBS/T in each tube.
4. Add one drop of undiluted human serum (25 μl) and mix.
5. Incubate at 37° C. for 1 h.
6. Tube is emptied by aspiration and washed 4× with 500 μl of PBS/T.
7. 100 μl of $I^{125}$ anti-human IgG is added to each tube. Incubate at 37° C. for 1 h.
8. Empty the tube by aspiration.
9. Wash carefully 5× with PBS/T.
10. The tubes are counted in a gamma counter.

EXAMPLE VII

Immunofluorescence Test

The strips are coated as in Example V.
A. Execution of the Test
1. Remove the dip strip from the antigen solution.
2. Place in a tube containing PBS/T and wash by shaking for 5 minutes.
3. Transfer to a tube containing serum to be tested.
4. Incubate at RT for 30 min.
5. Transfer to PBS/T and wash for 5 min.
6. Place in a tube containing working conc. of antihuman IgG labelled with fluorescein isothiocyanate.
7. Incubate for 30 min. at RT.
8. Wash as in 5.
9. Measure the fluorescence in a fluorimeter.
10. The serum is considered positive or negative by comparison with known controls.

EXAMPLE VIII

Countercurrent Immunoelectrophoresis

1. Microscopic slides are coated with 1% agarose in B-2 buffer ionic strength 0.025 pH 8.6.
2. Wells 6 mm in diameter are cut in the agar 6 mm apart.
3. The anodal well is filled with the patient sera and the cathodal end is filled with B.2 buffer ionic strength 0.025.
4. The tank is filled with B-2 buffer ionic strength 0.075.
5. The test is run for 30 min. at 6 mA/tray (each tray holds 6 slides).
6. The antigen at a concentration of 5 mg/ml is added to the cathodal well.
7. Electrophorisis is continued for an additional 2 hrs.
8. The slides are examined for formation of a precipitation line which indicate a positive reaction.
9. Slides may be washed and stained to improve sensitivity.

EXAMPLE IX

Complement Fixation Test (Lannette Micro-Kolmer Complement fixation test)

A. Determination of CF Unit of antigen

In a block filtration with known positive and known negative serum determine the highest dilution of antigen showing 3× or 4× fixation with the highest dilution of the immune serum. This is one unit of antigen. For test proper use 2 units of antigen in a volume of 0.025 ml.

B. Filtration of hemolysin
1. In six 11×75 Mm tubes place 0.2 ml of hemolysin diluted 1:6000 to 1:25,000 0.2 ml complement diluted 1:60, 0.2 ml sheep red blood cells (SRBC) suspension 1.4%, and 0.4 ml of diluent.
2. Label one tube as cell control and in it place 0.2 ml of SRBC and 0.8 ml of diluent.
3. Shake all seven tubes and incubate in a 37° C. water bath for 30 min.

4. Read for hemolysis.

The highest dilution of hemolysin which shows complete hemolysis represents one unit.

Two complement units are used in the test.

C. Procedure

1. Prepare serial dilution of the patient serum from 1:2 to 1:2048 (0.025 ml volume).
2. Add 0.025 ml of optimal antigen dilution.
3. Add 0.25 ml of cold veronal buffered diluent-(VBD).
4. Mix and allow to stand of RT for 30 min.
5. Add appropriate volume to complement controls.
6. Add 0.05 ml of complement and 0.05, 0.025 and 0.0125 to each test well.
7. Refrigerate for 15–18 hours.
8. Add 0.025 ml of sensitized SRBC, to each well and incubate at 37° C. for 30 min.
9. Centrifuge at 300× g for 3 min.
10. Complement Fixation—The reciprocal of the highest dilution showing 30% or less hemolysis is considered the CF titer.

What is claimed is:

1. A serological method for determining the presence of *Neisseria gonorrhoeae* antibodies in human serum which comprises preparing a composition containing undiluted serum or diluted in a physiologically acceptable liquid at a dilution of about 1:2 to 1:1000, incubating with a composition containing a species specific antigen preparation produced from a growth culture of *Neisseria gonorrhoea* to form an antigen-antibody conjugate when said antibodies are present; and detecting the presence of said conjugate; the antigen being protein in nature and characterized as follows:

1. stable in boiling water for a period of one hour,
   2. stable in an aqueous medium at pH values of 3–11,
   3. stable when incubated with the following enzymes;
      DNA—ase
      RNA—ase
      dextransase
      neuraminidase
      lysosyme,
   4. isoelectric point of 4±0.2,
   5. molecular weight of active subunits of 37,000–40,000 as determined by SDS-polyacrylamide gel,
   6. contains 2–3% organic phosphorous,
   7. soluble in water, and more soluble in aqueous media containing surface active agents; and insoluble in methanol, chloroform, and acetone,
   8. reacts specifically with antibodies produced in rabbits against purified L-antigen,
   9. partially soluble in 5% to 10% trichloroacetic acid.

2. A serological method as in claim 1 wherein the presence of said conjugate is detected by reaction with an anti-human IgG labelled with a chemical which fluoresces when exposed to ultraviolet light.

3. A method of claim 2 wherein the chemical is selected from the group consisting of fluorescein, rhodamine and auramine.

4. A method as in claim 2 wherein the antigen is produced by a culture of *Neisseria gonorrhoeae* ATCC No. 21823.

5. A method as in claim 2 wherein the antigen is produced by a culture of *Neisseria gonorrhoeae* ATCC No. 21824.

6. A method as in claim 2 wherein the antigen is produced by a culture of *Neisseria gonorrhoeae* ATCC No. 21825.

7. A Serological method as in claim 1 wherein the presence of said conjugate is detected by reaction with an anti-human IgG labelled with an enzyme.

8. A method as in claim 7 wherein the enzyme is selected from the group consisting of peroxidase, B-glucuronidase, B-D-glucosidase, B-D-galactosidase, urease, glucose oxidase plus peroxidase, galactose oxidase plus peroxidase, and acid phosphatase.

9. A method as in claim 7 wherein the antigen is produced by a culture of *Neisseria gonorrhoeae* ATCC No. 21823.

10. A method as in claim 7 wherein the antigen is produced by a culture of *Neisseria gonorrhoeae* ATCC No. 21824.

11. A method as in claim 7 wherein the antigen is produced by a culture of *Neisseria gonorrhoeae* ATCC No. 21825.

12. A serological method as in claim 1 wherein the presence of said conjugate is detected by reaction with an anti-human IgG labelled with a radioactive element.

13. A method as in claim 12 wherein the radioactive element is selected from the group consisting of $14_C$, $125_I$, $131_I$, and $35_S$.

14. A method as in claim 12 wherein the chemical is selected from the group consisting of fluorescein, rhodamine and auramine.

15. A method as in claim 14 wherein the antigen is produced by a culture of *Neisseria gonorrhoeae* ATCC No. 21823.

16. A method as in claim 14 wherein the antigen is produced by a culture of *Neisseria gonorrhoeae* ATCC No. 21824.

17. A method as in claim 14 wherein the antigen is produced by a culture of *Neisseria gonorrhoeae* ATCC No. 21825.

* * * * *